United States Patent

Sahatjian

[11] Patent Number: 5,954,706
[45] Date of Patent: *Sep. 21, 1999

[54] DRUG DELIVERY

[75] Inventor: Ronald A. Sahatjian, Lexington, Mass.

[73] Assignee: Boston Scientific Corporation, Natick, Mass.

[ * ] Notice: This patent is subject to a terminal disclaimer.

[21] Appl. No.: 08/473,136

[22] Filed: Jun. 7, 1995

Related U.S. Application Data

[63] Continuation of application No. 08/097,248, Jul. 23, 1993, Pat. No. 5,674,192, which is a continuation-in-part of application No. 07/795,976, Nov. 22, 1991, Pat. No. 5,304,121, which is a continuation-in-part of application No. 07/635,732, Dec. 28, 1990, abandoned.

[51] Int. Cl.$^6$ .................................................. A61M 31/00
[52] U.S. Cl. ............................................. 604/509; 604/96
[58] Field of Search ................................ 604/20, 28, 53, 604/96, 99, 101, 265, 266, 93, 43; 606/192, 194

[56] References Cited

U.S. PATENT DOCUMENTS

| | | |
|---|---|---|
| 3,699,956 | 10/1972 | Kitrilakis et al. . |
| 4,026,296 | 5/1977 | Stoy et al. . |
| 4,299,226 | 11/1981 | Banka . |

(List continued on next page.)

FOREIGN PATENT DOCUMENTS

| | | |
|---|---|---|
| 0 166 998 B1 | 1/1986 | European Pat. Off. . |
| 0 372 088 A1 | 6/1990 | European Pat. Off. . |
| 0 379 156 A2 | 7/1990 | European Pat. Off. . |
| 0 399 712 A1 | 11/1990 | European Pat. Off. . |
| 0 441 516 A2 | 8/1991 | European Pat. Off. . |
| A 380205 | 1/1924 | Germany . |
| DT 196327 | 7/1965 | Germany . |
| 53-006430 | 1/1978 | Japan . |
| 54-35036 | 10/1979 | Japan . |
| 1069826 | 1/1984 | U.S.S.R. . |
| 2112646 | 7/1983 | United Kingdom . |
| WO 89/12478 | 12/1989 | WIPO . |
| WO 91/05816 | 5/1991 | WIPO . |
| WO 91/08790 | 6/1991 | WIPO . |
| WO 92/11895 | 7/1992 | WIPO . |
| WO 92/11896 | 7/1992 | WIPO . |
| WO 92/13566 | 8/1992 | WIPO . |
| WO 92/15282 | 9/1992 | WIPO . |
| WO 93/11751 | 6/1993 | WIPO . |

OTHER PUBLICATIONS

Chapman et al., "A Bioabsorbable Stent: Initial Experimental Results", *Circulation* (Supp III) 82:0283 (abstract) (Oct. 1990).

Guyton et al., "Inhibition of Rat Arterial Smooth Muscle Cell Proliferation by Heparin: In Vivo Studies with Anticoagulant and Nonanticoagulant Heparin," *Cir. Res.* 46:625–634 (May 1980).

(List continued on next page.)

*Primary Examiner*—Ronald Stright
*Assistant Examiner*—A. T. Nguyen
*Attorney, Agent, or Firm*—Fish & Richardson P.C.

[57] ABSTRACT

The invention features a catheter and methods for delivering drug to tissue at a desired location of the wall of a body lumen. The catheter is constructed for insertion in a body lumen and has a catheter shaft and an expandable portion mounted on the catheter shaft. The expandable portion is expandable to a controlled pressure to fill the cross-section of the body lumen and press against the wall of the body lumen. In one embodiment, at least a portion of the exterior surface of the expandable portion is defined by a coating of a tenaciously adhered swellable hydrogel polymer. Incorporated in the hydrogel polymer is an aqueous solution of a preselected drug to be delivered to the tissue or plaque. The hydrogel polymer and drug are selected to allow rapid release of a desired dosage of the drug from the hydrogel polymer coating during compression of the hydrogel polymer coating against the wall of the lumen when the expandable portion is expanded. In other embodiments the polymer is released from the expandable portion in response to pressure, to coat the wall of the body lumen.

18 Claims, 5 Drawing Sheets

U.S. PATENT DOCUMENTS

| | | |
|---|---|---|
| 4,330,497 | 5/1982 | Agdanowski . |
| 4,364,392 | 12/1982 | Baran . |
| 4,423,725 | 1/1984 | Baran et al. . |
| 4,448,195 | 5/1984 | LeVeen et al. . |
| 4,481,323 | 11/1984 | Sterling . |
| 4,515,593 | 5/1985 | Norton ................................... 604/265 |
| 4,589,873 | 5/1986 | Schwartz et al. ...................... 604/265 |
| 4,592,340 | 6/1986 | Boyles . |
| 4,603,152 | 7/1986 | Laurin et al. ........................... 604/265 |
| 4,693,243 | 9/1987 | Buras . |
| 4,714,460 | 12/1987 | Calderon . |
| 4,732,930 | 3/1988 | Tanaka et al. . |
| 4,769,013 | 9/1988 | Lorenz et al. .......................... 604/265 |
| 4,784,647 | 11/1988 | Gross ..................................... 604/178 |
| 4,820,270 | 4/1989 | Hardcastle et al. ...................... 604/96 |
| 4,832,688 | 5/1989 | Sagae et al. ............................ 604/101 |
| 4,876,126 | 10/1989 | Takemura et al. . |
| 4,909,258 | 3/1990 | Kuntz et al. ............................ 128/658 |
| 4,923,450 | 5/1990 | Maeda et al. ........................... 604/265 |
| 4,950,256 | 8/1990 | Luther et al. ............................ 604/265 |
| 4,983,166 | 1/1991 | Yamawaki ................................ 604/96 |
| 4,993,412 | 2/1991 | Murphy-Chutorian ..................... 606/7 |
| 4,994,033 | 2/1991 | Shockey et al. ........................ 604/101 |
| 5,021,044 | 6/1991 | Sharkawy ................................. 604/53 |
| 5,026,607 | 6/1991 | Kiezulas . |
| 5,041,100 | 8/1991 | Rowland et al. ....................... 604/265 |
| 5,047,045 | 9/1991 | Arney et al. ............................ 604/194 |
| 5,049,132 | 9/1991 | Shaffer et al. .......................... 604/101 |
| 5,091,205 | 2/1992 | Fan ......................................... 604/265 |
| 5,102,402 | 4/1992 | Dror et al. ............................... 604/265 |
| 5,120,322 | 6/1992 | Davis et al. ............................. 604/265 |
| 5,135,516 | 8/1992 | Sahatjian et al. ....................... 604/265 |
| 5,163,906 | 11/1992 | Ahmadi .................................. 604/101 |
| 5,180,366 | 1/1993 | Woods ..................................... 604/96 |
| 5,213,576 | 5/1993 | Abiuso et al. ............................ 604/96 |
| 5,213,580 | 5/1993 | Slepian et al. ............................ 6623/1 |
| 5,232,444 | 8/1993 | Just et al. ................................. 604/96 |
| 5,234,456 | 8/1993 | Silvestrini ............................ 604/96 X |
| 5,304,121 | 4/1994 | Sahatjian ................................. 604/53 |

OTHER PUBLICATIONS

Ilmain et al., "Volume Transition in a Gel Driven by Hydrogen Bonding", 1991, *Nature,* 349:400–401.

Irie et al., "Stimuli–responsive polymers: chemical induced reversible phase separation of an aqueous soution of poly(N–isopropylacrylamide) with pendent crown ether groups", 1993, *Polymer,* 34(21):4531–35.

Langer, "Drug Delivery," IUPAC Meeting, Montreal, Canada (Jul. 12, 1990).

Mamada et al., "Photoinduced Phase Transition of Gels", 1990, *Macromolecules,* 23:1517–19.

McMath et al., "Experimental Application of Bioprotective Materials to Injured Arterial Surfaces with Laser Balloon Angioplasty", *Circulation* (Supp. III) 82:0282 (abstract) (Oct. 1990).

Suzuki et al., "Phase Transition in Polymer Gels Induced by Visible Light", 1990, *Nature,* 346:345–47.

Tarcha, "Diffusion Controlled Systems: Hydrogels", *Polymers for Controlled Drug Delivery,* CRC Press, Inc., 1991, Ch. 2, pp. 16–37.

Thompson et al., "Heparin and Growth Control of Vascular Cells," *Ann. N.Y. Acad. Sci.* 556:255–267 (1989).

Tidd et al., "Comparison of Hydrophilic Polymer–Coated Latex, uncoated Latex and PVC Indwelling Balloon Catheters in the Prevention of Urinary Infection," *J.Urol.* 48:285–291 (1976).

Tokuhiro et al., "NMR Study of Poly(N–isopropylaacrylamide) Gels near Phase Transition", 1991, *Macromolecules,* 24:2936–43.

Waller B.F. et al., "Vessel Wall Pathology After Angioplasty", CARDIO, Aug. 1990, p. 57, 70–72, 81.

Waller et al., "Morphologic Observations Late after Coronary Balloon Angioplasty" Mechanisms of Acute Injury and Relationship to Restenosis, *Radio.* 174:961–967 (Mar. 1990).

Wolinsky H. et al., "Local Introduction of Drugs into the Arterial Wall: A Percutaneous Catheter Technique", Journal of Interventional Cardiology, vol. 2, No. 4, 1989, pp. 219–228.

The Andreas Gruentzig Cardiovascular Center News Letter (Spring 1990).

Supplementary European Search Report, EP 92 90 3283, mailed Sep. 15, 1993.

International Search Report for PCT/US91/09804, mailed Apr. 8, 1992.

International Search Report for PCT/US91/09805, mailed Apr. 8, 1992.

International Search Report for PCT/US94/08394, mailed Dec. 23, 1994.

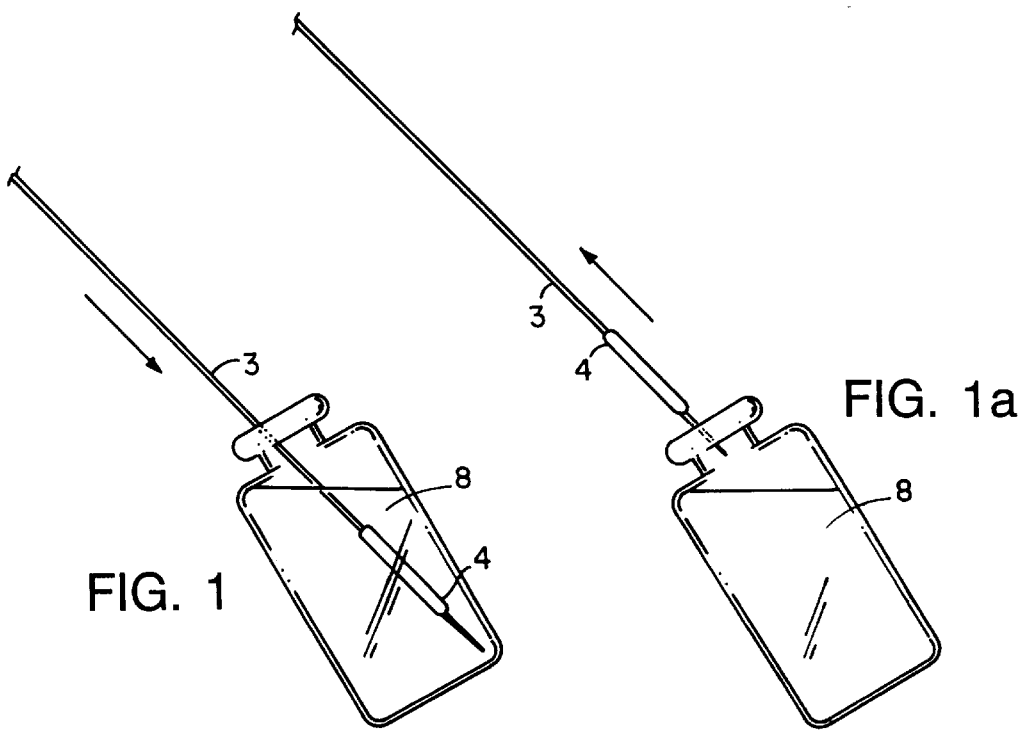
FIG. 1a
FIG. 1
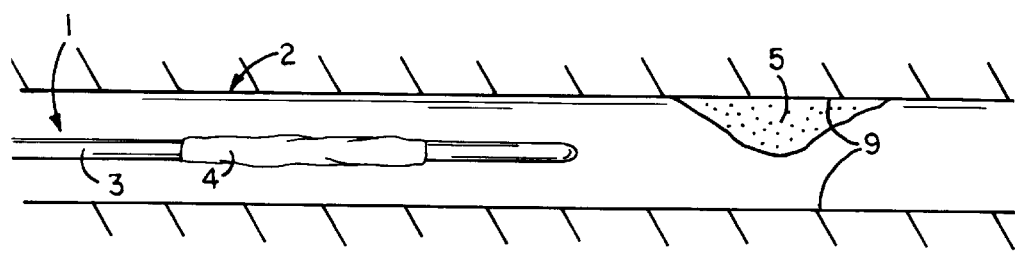
FIG. 1b
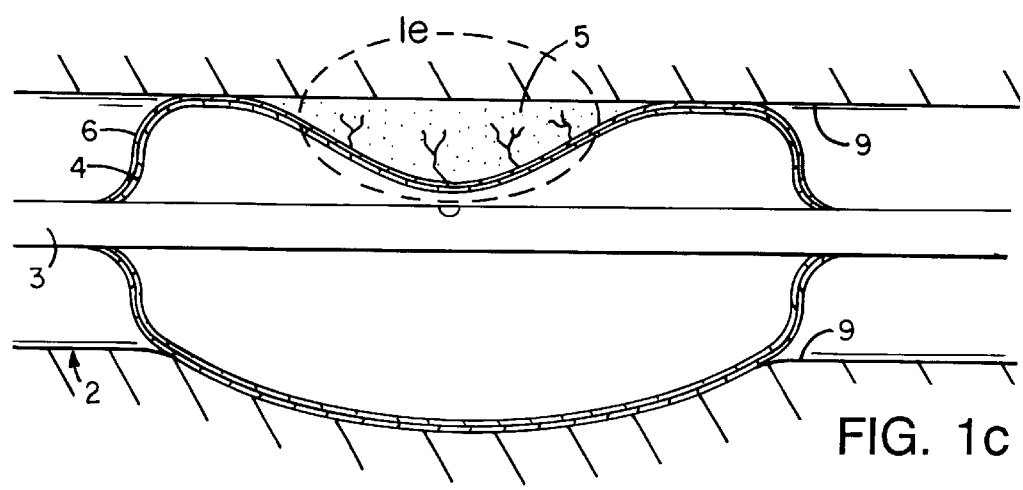
FIG. 1c

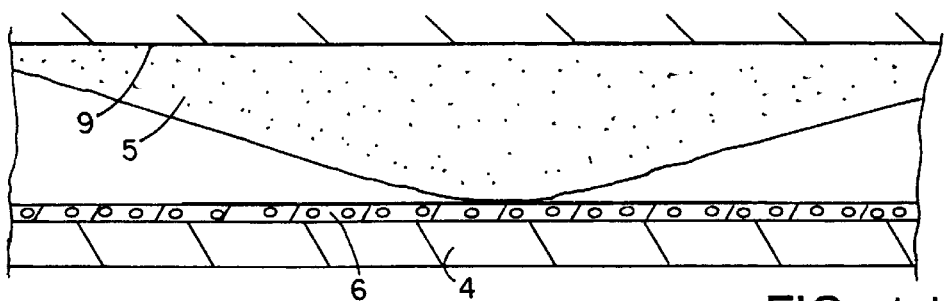
FIG. 1d
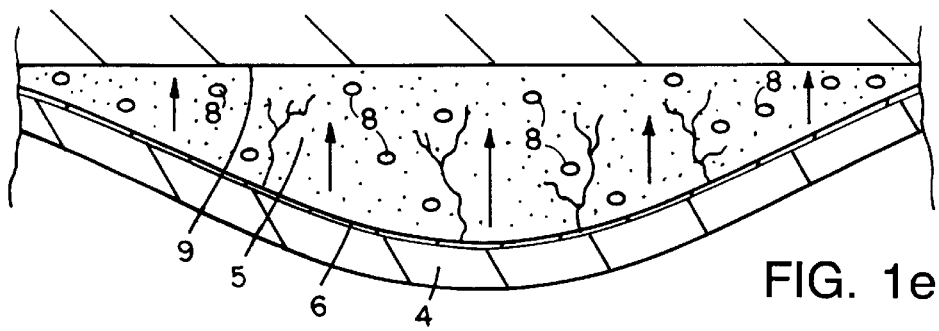
FIG. 1e
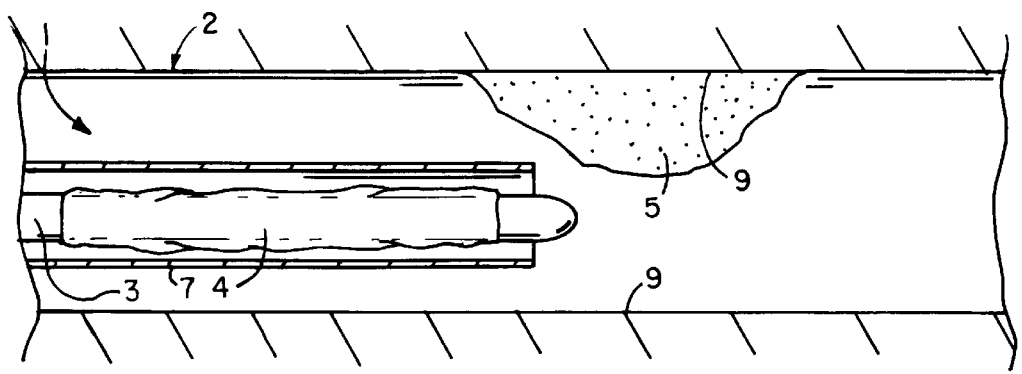
FIG. 2
FIG. 2a
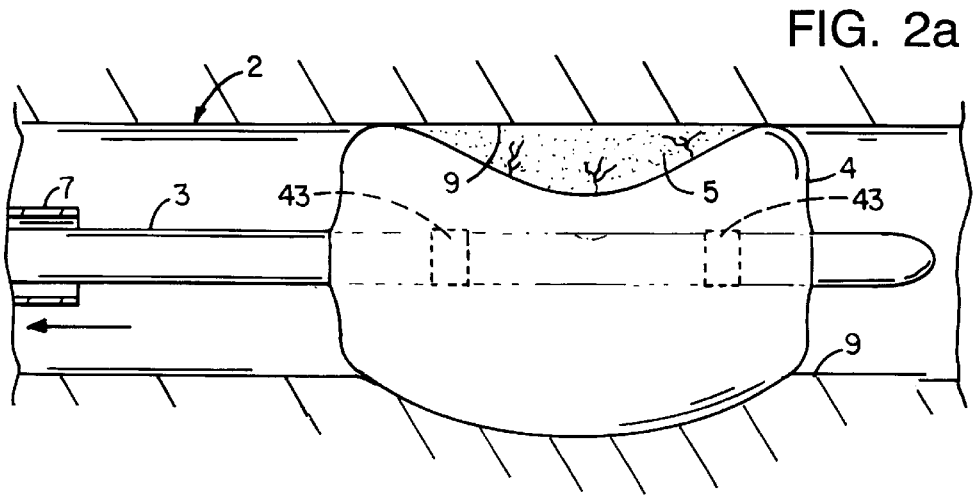

DRUG DELIVERY

CROSS REFERENCE

This is a continuation of application Ser. No. 08/097,248, filed on Jul. 23, 1993, now U.S. Pat. No. 5,674,192, which is a continuation-in-part of application, Ser. No. 07/795,976, titled "Drug Delivery System", filed Nov. 22, 1991, now U.S. Pat. No. 5,304,121, which is a continuation-in-part of application Ser. No. 07/635,732, now abandoned, titled Balloon Drug Delivery System, filed Dec. 28, 1990.

FIELD OF THE INVENTION

The invention relates to delivery of drugs to the walls of body lumens and other parts of the body.

BACKGROUND OF THE INVENTION

Systemic administration of drugs treats the organism as a whole, even though the disease may be localized, such as occlusion of a duct or vessel. Localization of a drug poses special problems in cases involving the walls of ducts and vessels, since, by nature, these organs serve as transport systems.

Atherosclerotic disease, for example, causes localized occlusion of the blood vessels resulting from the build-up of plaque. As the deposits increase in size, they reduce the diameter of the arteries and impede blood circulation. Angioplasty, which involves the insertion of catheters, such as balloon catheters, through the occluded region of the blood vessel in order to expand it, has been used to treat atherosclerosis.

The aftermath of angioplasty in many cases is problematic, due to restenosis, or closing of the vessel, that can occur from causes including mechanical abrasion and the proliferation of smooth muscle cells stimulated by the angioplasty treatment. Restenosis may also occur as a result of clot formation following angioplasty, due to injury to the vessel wall which triggers the natural clot-forming reactions of the blood.

In addition to the need for improved drug delivery in respect of angioplasty, and other treatments of ducts and vessels, their is need, more generally, for improved localized internal delivery of drugs in most branches of medicine for most types of drugs. In particular, there is need for improved delivery into tissue and into cells themselves within organs of the body via luminal and percutaneous access.

SUMMARY OF THE INVENTION

In one aspect, the invention features a catheter and method for delivering drug to tissue at a desired location in the body such as, the wall of a body lumen. The catheter is constructed for insertion in the body and has a catheter shaft and an expandable portion mounted on the catheter shaft. The expandable portion is expandable to a controlled pressure against the body tissue, e.g., or to fill the cross-section of the body lumen and press against the wall of the body lumen. At least a portion of the exterior surface of the expandable portion is defined by a coating of a tenaciously adhered swellable hydrogel polymer. Incorporated in the hydrogel polymer is an aqueous solution of a preselected drug to be delivered to the tissue. The hydrogel polymer and drug are selected to allow rapid release of a desired dosage of the drug from the hydrogel polymer coating during compression of the hydrogel polymer coating against the tissue or wall of the lumen when the expandable portion is expanded.

Various embodiments may include one or more of the following features. The catheter is adapted for insertion in a blood vessel, and the expandable portion is an inflatable dilatation balloon adapted for inflation at pressures in the range for effecting widening of a stenosed blood vessel. The pressure is in the range of about 1 to 20 atmospheres. The hydrogel polymer and drug are effective to release about 20% or more of the drug during inflation in the pressure range. The compression is effective to deliver the drug over a duration of about 10 minutes or less. The hydrogel polymer coating is about 10 to 50 microns thick in the swelled, uncompressed state. The hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides. The hydrogel polymer is polyacrylic acid. The drug is an anti-thrombogenic drug selected from the group consisting of heparin, PPACK, enoxaprin, aspirin and hirudin. The drug is an anti-proliferative drug selected from the group consisting of monoclonal antibodies, capable of blocking smooth muscle cell proliferation, heparin, angiopeptin and enoxaprin. The expandable portion is adapted for application of heat to the polymer material to control the rate of administration. The catheter further comprises a sheath member, extendable over the balloon to inhibit release of the drug into body fluids during placement of the catheter. The balloon catheter is a perfusion catheter having an expandable balloon. The expandable portion includes a stent, mountable in the blood vessel by expansion thereof. The drug is bound in the hydrogel polymer for slow time release of the drug after the compression of the hydrogel polymer by the expansion. The hydrogel polymer is a polyacrylic acid including an ammonium anion and the drug is heparin. The stent is expandable by a balloon. The stent and the balloon both include the swellable hydrogel coating incorporating the drug. The expandable portion of the catheter is prepared by introducing an aqueous solution of the drug to the hydrogel polymer coating, the catheter is introduced to the body or body lumen to position the expandable portion at the point of desired drug application, and the expandable portion is expanded to enable delivery of the drug by compression of the hydrogel polymer coating against the body tissue of the wall at the body lumen. The expandable portion is positioned at a point of occlusion in a blood vessel and the expandable portion is expanded at pressures sufficient to simultaneously dilate the vessel and deliver the drug by compression of the hydrogel polymer coating.

In a particular aspect, the invention includes a balloon catheter for delivering drug to tissue at a desired location of the wall of a blood vessel. The catheter is constructed for insertion in a blood vessel and has a catheter shaft and an expandable dilatation balloon mounted on the catheter shaft. The expandable balloon is expandable by an expansion controller to engage the tissue at a controlled pressure in the range of about 1 to 20 atmospheres to fill the cross-section of the blood vessel and press against the wall of the blood vessel. At least a portion of the exterior surface of the expandable balloon is defined by a coating of a tenaciously adhered swellable hydrogel polymer with a thickness in the range of about 10 to 50 microns in the swelled state, and incorporated within the hydrogel polymer coating is an aqueous solution of a preselected drug to be delivered to the tissue. The hydrogel polymer and drug are selected to allow rapid release of a desired dosage of about 20% or more of the drug solution from the hydrogel polymer coating during compression of the hydrogel polymer coating against body tissue or the wall of the vessel when the expandable portion is expanded in the pressure range.

In various embodiments of this aspect of the invention, the hydrogel polymer is also selected from the group consisting of polycarboxylic acids, cellulosic polymers, gelatin, polyvinylpyrrolidone, maleic anhydride polymers, polyamides, polyvinyl alcohols, and polyethylene oxides. The hydrogel polymer is polyacrylic acid. The drug is an anti-thrombogenic drug selected from the group consisting of heparin, PPACK, enoxaprin, aspirin and hirudin. The drug is an anti-proliferative drug selected from the group consisting of monoclonal antibodies capable of blocking smooth muscle cell proliferation, heparin, angiopeptin and enoxaprin. The catheter further comprises a sheath member, extendable over the balloon to inhibit release of the drug into body fluids during placement of the catheter.

In another aspect of the invention, the invention also features a catheter for delivering drug to tissue at a desired location of the body or wall of a body lumen. The catheter a catheter shaft and an expandable portion mounted on the catheter shaft, the expandable portion being expandable to a controlled pressure, e.g., to fill the cross-section of the body lumen and press against the wall of the body lumen. At least a portion of the exterior surface of the expandable portion is defined by a coating of a body-fluid soluble polymer, and incorporated within the soluble polymer, a preselected drug to be delivered to the tissue. The soluble polymer and drug are selected to allow release of the polymer from the surface of the balloon during compression of the polymer coating against the wall of the body lumen when the expandable portion is expanded to coat the wall of the body lumen.

Various embodiments of this aspect of the invention include the following. The polymer is selected from the group consisting of polycaprolactone, polyorthoesters, polylactic acids, polyglycolic acids, and albumin. The drug is selected from anti-thrombogenic drugs, anti-proliferative drugs and thrombolytic drugs or may be a mixture thereof. Such drugs can be delivered either simultaneously or sequentially to a desired location in the body. The drug can also be a cytotoxic drug.

In other embodiments, the drug is a naked nucleic acid or a nucleic acid incorporated into a viral vector. By naked nucleic acid is meant a uncoated single or double stranded DNA or RNA molecule not incorporated into a virus or liposome.

The expandable portion of the catheter can be adapted for application of heat to the polymer material to control the rate of administration. The polymer is a meltable polymer, and the release of the polymer is aided by the application of heat. The catheter comprises a sheath extendable over the balloon to inhibit release of drug into the body fluids during placement of said catheter. The sheath can be made of polyethylene or polyurethane. The sheath may contain a slit at the distal end to facilitate movement of the balloon in and out of the sheath. In other embodiments, the sheath may be flexible and sized to tightly surround the balloon in its deflated or slightly inflated state.

A coating such as a water soluble polymer, e.g., carbowax, gelatin, polyvinyl alcohol, polyethylene oxide or polyethylene glycol, or a biodegradable or thermally degradable polymer, e.g., albumin or pluronic gel F-127 can be used as a protective covering over the balloon to prevent release of the drug from the hydrogel until it is delivered to the desired location in the body.

In general, an advantage of the invention is the application of drugs by active diffusion directly into the tissue within the body requiring treatment penetration or impregnation of the drug into the tissue being added by the pressure applied by the balloon. The drug is preferably applied in a rapid but low-stress, low energy manner that does not further injure the tissue to be treated, and administration is selectively and evenly distributed over the treated area such that the drug can be taken up by tissue and plaque, without, e.g., being washed away by body fluids.

Further aspects of the invention, in some instances accompanied by experimental results, will now be presented. For the various experiments the same hydrogel coating as described above as being preferred, was employed, made with a coated thickness within the tolerance limits of 2 to 5 microns. In each case it was observed that the technique of the invention caused the drug or particles containing the drug to be impregnated into the tissue or thrombus well below the surface.

DESCRIPTION OF PREFERRED EMBODIMENTS

We first briefly describe the drawings.

DRAWINGS

FIGS. 1–1a are enlarged views of a method of preparing an embodiment of the invention.

FIG. 1b is an enlarged cross-sectional view of an embodiment of the drug delivery balloon catheter of the invention being moved through a vessel toward an occlusion to be treated.

FIG. 1c is an enlarged cross-sectional view of the balloon in FIG. 1b, now fully inflated and at the site of occlusion.

FIG. 1d is a further enlarged, schematic cross-sectional view of the portion of FIG. 1c indicated in the circle 1e, but taken prior to full inflation.

FIG. 1e, which corresponds to the portion of FIG. 1c indicated in the circle 1e, is an enlarged, schematic cross-sectional view, as in FIG. 1d, but with the balloon under full inflation to release the drug coated on the balloon.

FIG. 2 is an enlarged cross-sectional view of another embodiment of the drug delivery balloon catheter of the invention including a sheath for covering the catheter as it is being moved through a vessel toward the occlusion to be treated.

FIG. 2a is an enlarged cross-sectional view of the catheter of FIG. 2 with the sheath retracted and balloon inflated at the site of occlusion.

Figure 2B:
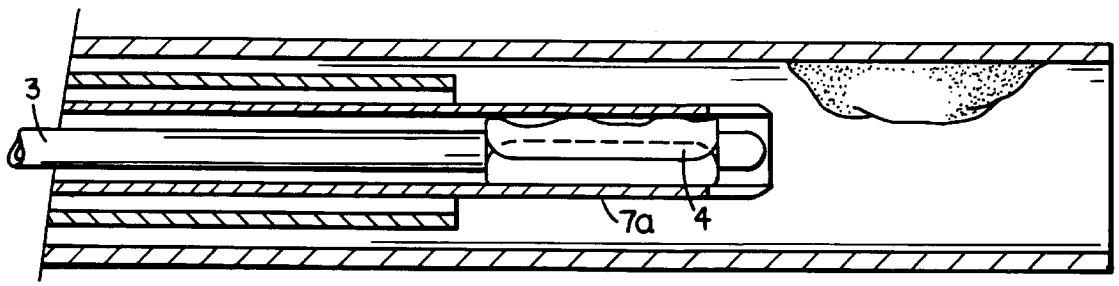
Figure 2C:
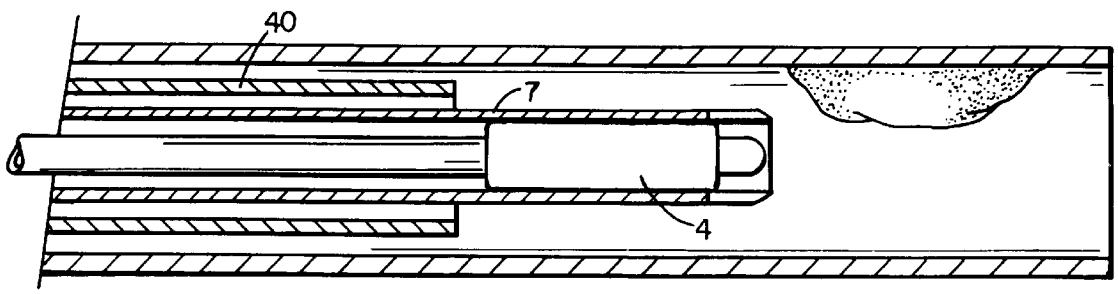

FIG. 2b is a diagrammatic cross-sectional view showing a close-fitting retractable sheath covering the drug-laden hydrogel coating on the balloon of an angioplasty balloon catheter;

FIG. 2c is a view similar to FIG. 2b of an alternative embodiment in which the sheath is not so closely fitting, the balloon being slightly inflated to engage the coating in a low-pressure protective relationship with the sheath.

Figure 2E:
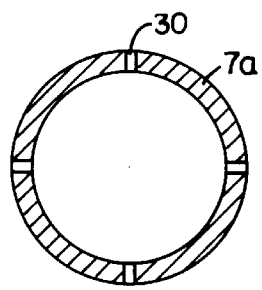
Figure 2D:
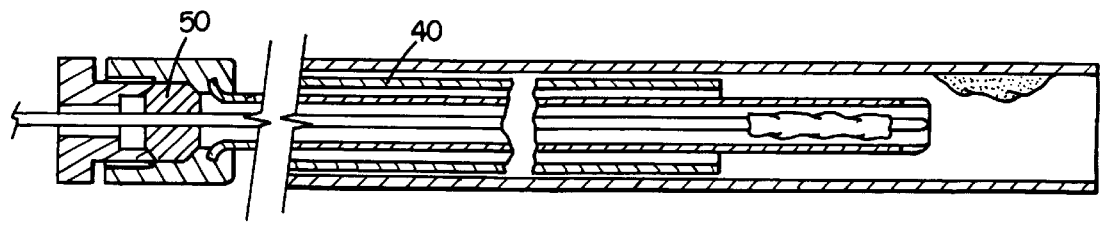

FIG. 2d is a view similar to FIG. 2c having a distal seal for preventing outward flow of blood along the balloon during insertion to limit the eluting effect of blood as the catheter is inserted;

FIG. 2e is a transverse cross-sectional view illustrating slits in the distal end of the catheter that render its walls more flexible to enable the balloon to more readily be withdrawn into the sheath.

Figure 3:
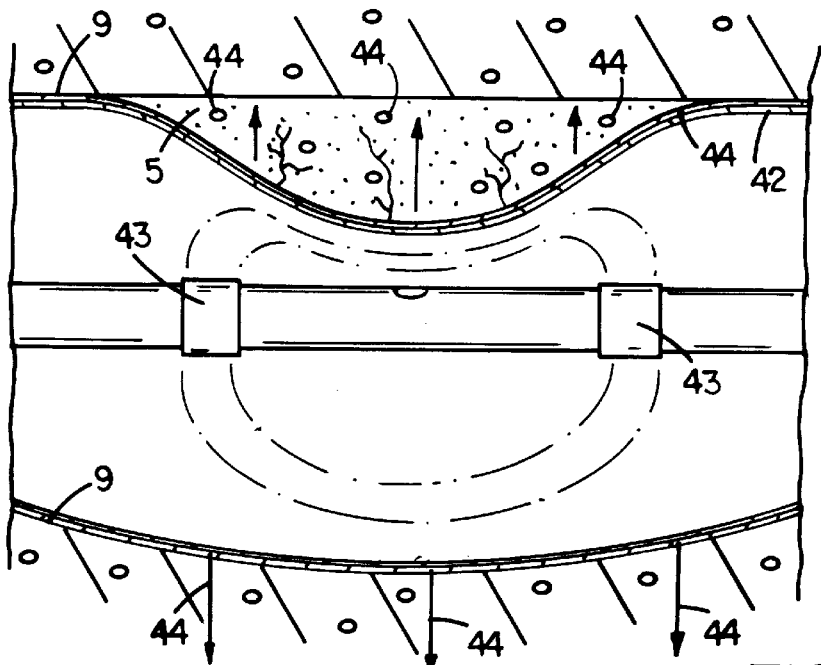

FIG. 3 is an enlarged, schematic cross-sectional view of another embodiment of the drug delivery balloon catheter in which the drug, originally held within a polymer applied to a thermal balloon of the invention, is now entering the surrounding tissue.

Figure 3A:
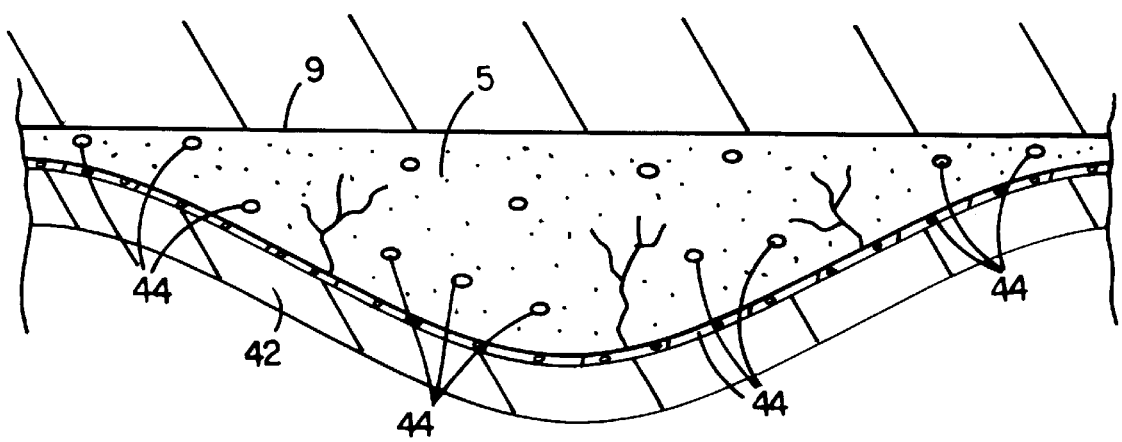

FIG. 3a is a further enlarged, schematic illustration of the embodiment of FIG. 3 and illustrates the entry of the drug, shown as circles, into the surrounding tissue.

Figure 4:
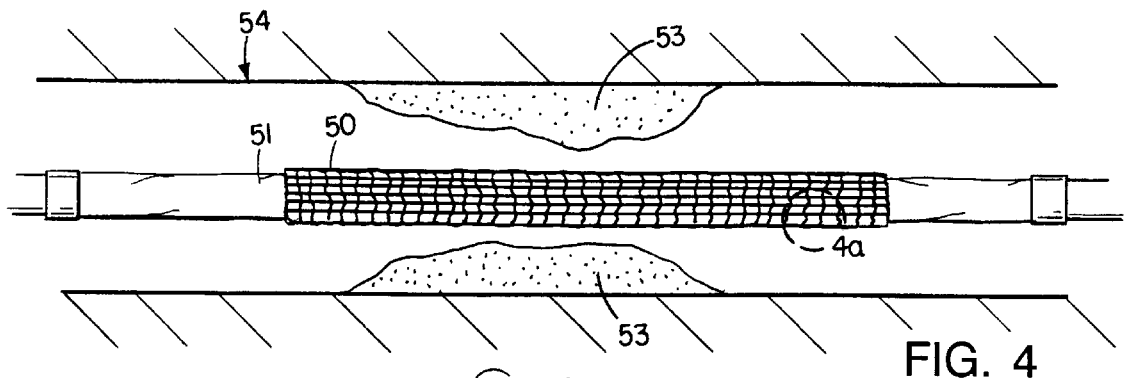

FIG. 4 shows a balloon catheter with a hydrogel and drug coated endoprosthesis mounted on the balloon section, in the region of the thrombus, before radial expansion of the balloon section and endoprosthesis.

Figure 4A:
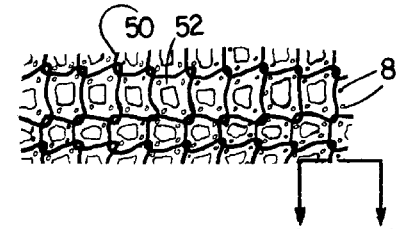
Figure 4B:
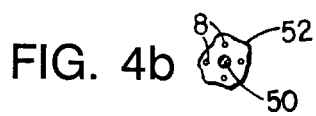

FIG. 4a is an enlargement of FIG. 4 showing the hydrogel polymer and drug coated endoprosthesis and FIG. 4b is a cross-section along the line b—b in FIG. 4a.

Figure 5:
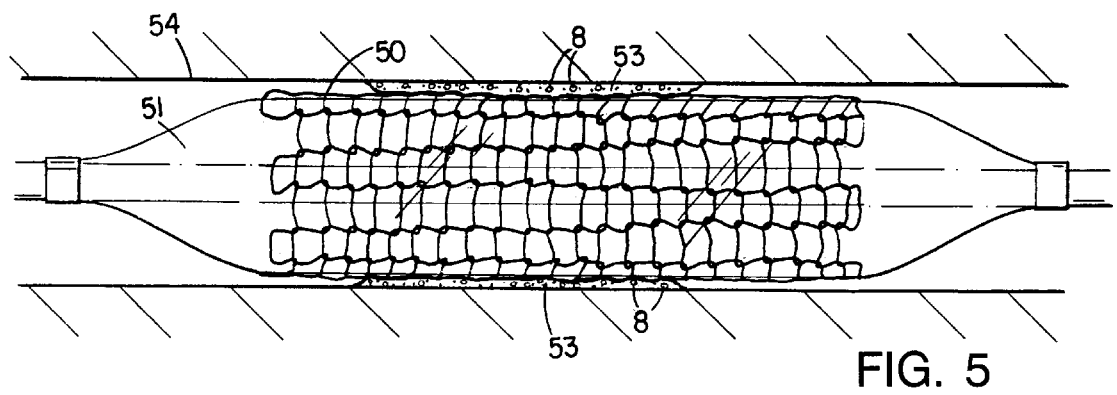

FIG. 5 shows the endoprosthesis compressed against the vessel wall by radial expansion of the balloon section with the drug diffused into the compressed thrombus before removal of the balloon catheter.

Figure 6:
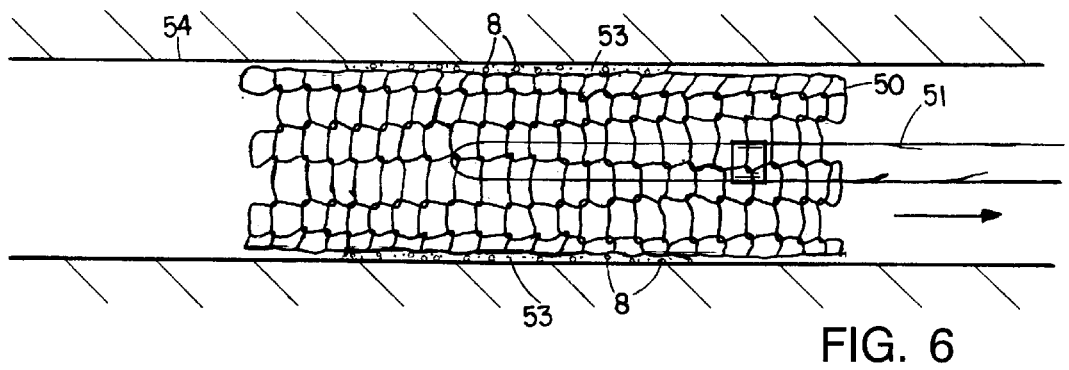

FIG. 6 shows the endoprosthesis positioned against the drug inside the compressed thrombus, after removal of the balloon catheter.

GENERAL DESCRIPTION

Referring to FIGS. 1–1e, in one embodiment, the invention includes a drug delivery balloon catheter device 1 comprising a catheter body 3 having a balloon 4 attached at its distal end. The balloon 4 on the catheter 3 includes a swellable hydrogel polymer coating 6. As shown in FIGS. 1–1a, a drug 8 in an aqueous solution is absorbed into the hydrogel with the balloon in the deflated state prior to insertion into the patient by the physician, e.g., the hydrogel-coated balloon may be immersed in a small tube or vial containing the drug. The drug may also be applied in the form of droplets, such as from an eyedropper, or the drug may be precipitated into the hydrogel prior to sterilization and sold as a finished device. Exposure of the hydrogel to the solution causes the hydrogel to swell.

As shown in FIG. 1b, typically the device 1 is inserted into the duct or vessel 2 having a region to be treated, such as an occlusion due to a deposition of plaque 5 on the vessel wall tissue 9. The device 1 is moved along the vessel to position the balloon 4 at the occlusion site, as shown in FIG. 1c. The vessel may be, for example, a narrow, tortuous opening through which the catheter is passed by torquing from the distal end. As the balloon is inflated the pressure created by the balloon against the tissue compresses the hydrogel and the drug is quickly and freely released for transfer into the plaque and tissue. The pressure applied to the fluid drug against the plaque and tissue by the expanded balloon during application of the drug enhances transfer of the drug into the tissue and plaque. The process is referred to here as "active diffusion". The balloon and catheter may be exposed to the body fluids of the lumen for a considerable time, e.g., up to about 15 minutes in some angioplasty procedures. An advantage of this invention is that large amounts of the drug, e.g., greater than 20%, even 30–50% or more, of the drug solution contained in the hydrogel, is diffused into the affected area in the short time duration in which the hydrogel is compressed, e.g., 2–10 minutes after the balloon is inflated at the treatment site (it has been found that dosage impregnated in the tissue as low as 1% of the drug content of the coating is sufficient to have therapeutic effects.) The inflation pressure needed to dilate the vessel which also results in the compression of the coating, is in the range of 1 to 20, typically about 2 to 10 atmospheres. The balloon is preferably a compliant material such as polyethylene which conforms to the shape of the lumen wall. The balloon may also be formed of other materials used in angioplasty, e.g., a nondistending material, such as polyethylene terephthalate (PET). Transporting the drug in the hydrogel prevents substantial release of the drug to body fluids prior to reaching the treatment area and allows large dosages to be delivered at a desired location during the drug application phase.

In the embodiment of FIG. 1c, the balloon coating 6 is a swellable, compressible coating formed of the hydrogel and drug in solution. In FIG. 1d, the balloon 4 is shown inflated such that the coating 6, which has an initial thickness, is in contact with the occlusion 5 but not under substantial pressure. Further inflation of the balloon 4, as shown in FIG. 1e, compresses the hydrogel coating 6 against the occluded areas 5 reducing the thickness of the coating as shown and causing quick release of the drug (represented by circles) contained in the coating 6 and impregnating it directly into the plaque and nearby healthy tissue, as indicated by the directional arrows, much in the nature of squeezing liquid from a sponge. The introduction of the drug into the plaque and tissue occurs simultaneously with opening of the occlusion by the dilatation balloon. Thus, as cracking of the plaque and stimulation of smooth muscle cells beneath the plaque and along healthy tissue of the vessel wall are caused by dilatation, a therapeutic drug is simultaneously applied to the affected area, e.g., to counteract the effects of the trauma. The thickness of the balloon 4 remains substantially the same, while the thickness of the coating 6 decreases due to the compression of the coating and the release of the drug 8. (FIGS. 1d–1e are schematic drawings and are not to scale with respect to the thickness of the balloon relative to the thickness of the hydrogel coating.) The drug carried by the balloon is evenly applied to plaque and tissue and isolated by the pressure of the balloon from the flow of body fluids in the lumen such that the drug, e.g., an anti-proliferative, may actively diffuse through the cracks formed in the plaque and reach the smooth muscle tissue. (It will also be understood that, as an alternative procedure, after dilation with a conventional angioplasty balloon catheter, a catheter carrying a drug-delivery, inflatable balloon, such as has been described, may be used to treat the vessel.)

The hydrogel coating is characterized by the ability to incorporate a substantial amount of the drug, typically in aqueous solution form, and is swellable such that the aqueous drug solution can be effectively squeezed out of the coating when pressure is applied by inflation of the balloon. Administration of the drug in this way enables the drug to be site-specific, such that release of high concentrations and/or highly potent drugs may be limited to direct application to the diseased tissue. Furthermore, the drug is applied to the diseased tissue by the sponge-like coating in an even, gentle manner without disrupting or injuring the healthy tissue, while diffusion of the drug into the tissue is facilitated by the application of the pressure of the inflated balloon. While this occurs the pressure also effectively forms a seal that prevents the flow of body fluids from washing the drug downstream of the treatment area. The dosage applied to the tissue may be controlled by regulating the time of presoaking the drug into the hydrogel coating to determine the amount of absorption of the drug solution by the hydrogel coating. Other factors affecting the dosage are the concentration of the drug in the solution applied to the coating and the drug-releasability of the hydrogel coating, determined by, for example, the thickness of the hydrogel coating, its resiliency, porosity and the ability of the hydrogel coating to retain the drug, e.g., electrostatic binding or pore size, or the ionic strength of the coating, e.g., changed by changing the pH.

The drug may be an anti-thrombogenic drug, such as heparin or a heparin derivative, PPACK (dextrophenylalanine proline arginine chloromethylketone)

or an anti-proliferative, such as heparin (also known to have anti-proliferative properties), enoxaprin, angiopeptin, or monoclonal antibodies capable of blocking smooth muscle cell proliferation, or it may be hirudin or acetylsalicylic acid (i.e., aspirin). Dosages applied to the tissue, for example, of heparin are typically in the range of 10–30 mg of heparin solution containing 200–1,000 units of sodium heparin. For use with hydrogels, the drug is preferably water soluble, so that the drug may be easily absorbed into the coating matrix.

The sponge-like characteristics of the hydrogel allows the aqueous drug solution to be effectively squeezed out of the coating when pressure is applied by inflation of the balloon. The hydrogel and drug combination are preferably noncomplexed, i.e., held together through the ability of the hydrogel to swell and absorb the drug solution, thereby allowing the preferable free-release of the drug at the treatment site.

In particular embodiments it may be advantageous to select a hydrogel coating for a particular drug such that the drug is not substantially released into body fluids prior to application of pressure by expansion of the balloon. Binding of the drug may also be accomplished by electrostatic attraction of the drug to the coating or a coating additive or by mechanical binding, e.g., employing a coating having a pore size that inhibits inward flow of body fluids or outward flow of the drug itself, that might tend to release the drug. Hydrogels are particularly advantageous in that the drug is held within the hydrogen-bond matrix formed by the gel.

The hydrogel is a cross-linked polymer material formed from the combination of a colloid and water. Cross-linking reduces solubility and produces a jelly-like polymer that is characterized by the ability to swell and absorb a substantial amount of the drug, typically in aqueous solution form. The hydrogel coating is also particularly hydrophilic, water swellable, and lubricious (i.e., having a low coefficient of friction). Preferred hydrogels are polyacrylic acid polymers available as HYDROPLUS® (Boston Scientific, Watertown, Mass.) and as described in U.S. Pat. No. 5,091,205, the portion disclosed in the parent application to this patent being hereby incorporated by reference).

Referring to U.S. Pat. No. 5,091,205 a balloon catheter to be coated with the hydrogel is first contacted with a polyisocyanate or diisocyanate in a liquid medium containing 0.6% isocyanate by weight coated and dried to give a surface which can subsequently be coated with a polycarboxylic acid in a liquid medium. The acid can be a polyacrylic acid and having the formula as shown below:

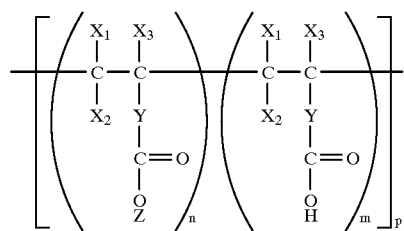

Where:

$n = 0$–$0.95$ mole fraction of neutralized acid moieties;

$m = 0.05$–$1.0$ mole fraction of acid moieties with the proviso that $n + m = 1$;

$X_1$, $X_2$, $X_3$ are each a hydrogen atom or a monovalent organic radical;

Y is a single bond or a divalent organic radical;

Z is a metallic ion or a tertiary ammonium ion; and p is a number such that the polymer has a molecular weight between 200,000 and about 5,000,000;

said carboxylic acid-containing polymer contained in at least one second inert organic solvent to provide a multiple coated substrate; and thereafter drying said multiple coated substrate to provide a hydrophilic, lubricious hydrogel.

The drug, e.g., heparin in aqueous solution, is absorbed into the coating without completing and is freely released therefrom. Such hydrogel-drug combinations deliver about half of the drug solution in response to pressures in the range employed for balloon angioplasty in the vascular system. In other particular embodiments, the hydrogel polymer includes acid groups and incorporates a drug which is anionic in nature that is bound by electrostatic attraction to cations in the coating, such as an ammonium cation, as described in "Lubricous Antithrombogenic Catheters, Guidewires, and Coatings," by Ronald Sahatjian et al., U.S. Ser. No. 7/451,507, filed on Dec. 15, 1989, now U.S. Pat. No. 5,135,516, the entire contents of which are hereby incorporated by reference. The coating incorporating the quaternary ammonium salt is effective to deliver an initial fast release of the drug during compression and a slow release of drug remaining in the compressed coating after compression. Such a coating is particularly useful for coating vascular stents as described further below.

In general, when dry, the hydrogel coating is preferably on the order of about 1 to 10 microns thick, with a 2 to 5 micron coating typical. Very thin hydrogel coatings, e.g., of about 0.2–0.3 microns (dry) and much thicker hydrogel coatings, e.g., more than 10 microns (dry), are also possible. Typically, the hydrogel coating thickness may swell by about a factor of 6 to 10 or more when the hydrogel coating is hydrated. For example, a hydrogel coating of about 1 to 3 microns thickness, when dry, usually swells to about 10–30 microns thickness, when hydrated. Most preferably, the thickness of the coating is about 10 to 50 microns in the swelled, uncompressed state, and incorporates about 20–30mg of drug solution.

Referring to FIG. 2, in another embodiment of a drug delivery balloon catheter, the catheter 3 is preferably very small in diameter and flexible, much in the nature of a guidewire, formed, in this case, of hollow tubing to which the coated balloon 4 is attached. The balloon is covered by a protective sheath 7 while the instrument 1 is inserted into the vessel or duct 2 and positioned at the treatment region. As the coated balloon 4 is positioned at the occluded site 5, (FIG. 2a) the protective sheath 7 is drawn back to expose the balloon 4. In an alternative embodiment, the sheath remains stationary while the guidewire-like catheter moves the coated balloon forward into the occluded region. The sheath 7 protects the coating and inhibits premature release of the drug. Such a sheath can be particularly advantageous with coatings and drugs where little substantial chemical or mechanical binding occurs between the drug and the coating. Additionally, the balloon catheter may be a thermal balloon catheter with electrodes 43, as more fully described below. The application of such heat may be employed to facilitate the release of the drug from the coating, to facilitate penetration of the drug into the tissue, or to facilitate the therapeutic action of the drug.

A procedure for preparing a drug delivery balloon with a hydrogel coating and an experiment of drug delivery for the above embodiments are presented in the following examples.

EXAMPLES

Example 1

A hydrogel coating on an angioplasty balloon may be formed as follows. The surface of the balloon (polyethylene)

of an angiographic catheter is prepared by wiping down with clean cloth. The balloon has an O.D. (outer diameter) of about 3.5 mm (inflated). The balloon is coated with a solution of 4,4' diphenylmethane diisocyanate (MDI) in methylethylketone for 30 minutes. After drying in an air oven at 85° C. for 30 minutes, the balloon is dipped in a 1.7% solution of poly(acrylic acid) homopolymer having a molecular weight of about 3,000,000 in dimethylformamide (DMF) and tertiarybutyl alcohol. After drying at about 85° C. for 30 minutes, a smooth coating is obtained. The balloon is oven dried for 8 hours at 50° C. One function of the drying steps is to remove solvent from the coating. The surface of the balloon becomes instantly lubricous upon exposure to water. The polyisocyanate solution is at a concentration of about 0.5 to 10% by weight. The polyacrylic acid is at a concentration of about 0.1 to 10% by weight. The poly (carboxylic acid) to polyisocyanate molar ratio is generally about 1:1. The formation of the hydrogel is further described in U.S. Pat. No. 5,091,205, incorporated supra.

A solution of heparin salt may be applied to the coating. The solution is 10,000 units heparin sodium injection (Fisher Scientific, Pittsburgh, Pa.) USP Grade (1000 units/ml which is then added to 650 cc distilled water) and may be applied by dipping for, e.g., about 1 minute at room temperature. The heparin does not form a complex with the hydrogel solution and is freely released in response to compression of the polymer.

After a catheter is prepared for use as discussed above, the catheter may be introduced into the patient using the Seldinger technique and expanded at a desired location to compress the hydrogel and deliver the heparin solution.

Example 2

Delivery of a drug from a hydrogel coating on a balloon was investigated in the following experiment. Tritium-labeled PPACK was absorbed into a 3.5 mm Slider® (balloon catheter from Boston Scientific Corporation) balloon coated with about a 40 micron thick (in the swelled state) coating as described in Example 1. The coating was dried and the radioactivity was counted. The balloon was then wetted with saline to swell the coating area. The balloon was inflated over a period of about one minute to about 4 atmospheres and held at this pressure for about 10 minutes in a thrombus created in an AV shunt from a balloon. The balloon was withdrawn and the amount of the drug in the thrombus was counted with a radiation counter. The experiment was performed with two different balloons using two different concentrations of PPACK, one balloon with 1–2 mg PPACK, and one balloon with 4mg PPACK. Both balloons delivered about 50% of the PPACK into the thrombus.

Other Embodiments

Referring to FIG. 3, in another embodiment, the drug 44 is held within a polymer coating applied to the exterior of a thermal balloon, central wall portions 42 of which are shown in FIG. 3. The balloon is positioned in the lumen in the region to be treated and inflated such that the polymer coating is in contact with the tissue as shown in FIGS. 3–3a. Heating of the balloon 42 melts the polymer and releases the drug 44 in a gentle, even, low-energy manner into the affected tissue. Suitable polymers include, but are not limited to, albumin, and collagen, e.g., gelatin, such as gel foams, which typically melt between about 40–60° C. or polyvinylpyrrolidone (PVP), which dissolves rapidly when heated. The thermal balloon typically operates between 40–80° C. A suitable heated balloon system for this embodiment or that of FIG. 2a is discussed in Lennox et al., "Heated Balloon Catheters and the Like," U.S. Pat. No. 4,955,377, hereby incorporated by reference. Inflating liquid is heated as a result of $I^2R$ losses by radiofrequency current flowing in the inflation fluid, e.g., saline, between the electrodes 43 (see FIGS. 2a and 3), the liquid in turn heating the balloon wall. In the alternative, drugs which melt and which could be applied either with a meltable or non-meltable polymer binder might be used.

An advantage to the meltable coatings is that the polymer may be cross-linked, (e.g., by physical or chemical cross-linking) after application of the drug 44 to the balloon to inhibit release of the drug 44 as the balloon 42 is introduced through the body lumen to the area of treatment. The polymer itself typically does not melt off the balloon, but rather softens in a manner permitting release. However, in embodiments where the polymer is bioabsorbable, e.g., polycaprolactone, polyorthoesters, polylactic acids, and polyglycolic acids, some or even all of the polymer may dissolve off of the balloon.

The balloon may also be coated with a polymer incorporating a drug and inflated to press against the wall of the body lumen, where the polymer is selected to separate from the balloon and coat the wall of the lumen, in response to such pressure with or without the application of heat from the balloon. After application of the polymer, the balloon can be deflated and removed. In this embodiment, the polymer may be a blood soluble polymer such as albumin, collagen or the like, incorporating a drug such as heparin. The polymer produces a smooth coating on the wall of the lumen and releases the drug to the tissue over time as the polymer dissolves. Other soluble polymers are meltable and bioabsorbable polymers discussed above.

In another embodiment (see FIGS. 4–6) an endoprosthesis (stent) is used in combination with a balloon catheter drug delivery system. An endoprosthesis 50 is placed over the balloon catheter 51, and then coated with a noncomplexed hydrogel coating 52. The drug 8, shown as circles, in aqueous solution is then absorbed into the hydrogel coating 52. The balloon 51 and hydrogel and drug coated endoprosthesis 50 are slid until they reach the region of the occlusion 53 in the vessel 54. This is shown in FIG. 4. An enlargement of the drug and hydrogel polymer coated endoprosthesis 50 is shown in FIGS. 4a and 4b (thickness of coating 52 is greatly exaggerated). After the balloon 51 and hydrogel and drug coated endoprosthesis 50 have been positioned inside the vessel 54, the endoprosthesis 50 is radially expanded by the admission of pressure to the balloon 51 and compressed against the vessel wall 54 with the result that occlusion 53 is compressed, and the vessel wall 54 surrounding it undergoes a radial expansion. The pressure from inflating the balloon squeezes the hydrogel 52, freely releasing the drug 8 into the tissue. The endoprosthesis 50 is held in position in the expanded state as shown in FIG. 5. The pressure is then released from the balloon and the catheter is withdrawn from the vessel. FIG. 6 shows the drug 8 inside the compressed thrombus with the endoprosthesis expanded and left in position, with the balloon catheter being withdrawn from the lumen. It will be understood that only the endoprosthesis may include the hydrogel polymer coating. In the embodiments employing a hydrogel-coated stent, the hydrogel and drug are selected such that an initial high dosage of drug is delivered to adjacent tissue upon initial compression of the polymer and thereafter a slow, sustained time-release of drug remaining in the hydrogel polymer occurs. Preferred hydrogel-drug combinations are those that employ a binding of the drug, such as electrostatic binding, e.g., by using a polyacrylic acid hydrogel in combination with an ammonium cation and heparin. In this case, the coating continues to release drug after expansion of the stent and removal of the balloon catheter. The stent may be a balloon-expansible stent as described above or a self-expanding stent, e.g., of the type formed with superelastic materials such as Nitinol.

Any of the embodiments discussed herein can be used with a protective sheath as described in FIGS. 2–2a. In addition, a heated balloon catheter may be used in all combinations of the embodiments above to enhance and control the rate of drug-solution delivery into tissue. Other compressible sponge-like polymers, e.g., non hydrogels which release drug solutions in response to pressure, might be used as described with respect to the embodiment of FIG. 1 et seq.

Further aspects of the invention, in some instances accompanied by experimental results, will now be presented. For the various experiments the same hydrogel coating as described above as being preferred was employed, made with a coating thickness within the tolerance range of 2 to 5 micron, measured in the dry state. In each case, it was observed that the technique of the invention caused the drug or particles containing the drug to be impregnated into the tissue or thrombus well below the surface.

One further aspect of the invention is a hydrogel-coated balloon as a local, pressurized delivery device for more efficient thrombolysis. In this embodiment, the hydrogel-coated balloon is impregnated with a thrombolytic agent. Examples include urokinase, pro-urokinase, streptokinase, and tissue plasminogen activator (tPA) and uses include patients having severe complications resulting from thrombus. Specific examples include patients with acute myocardial infarction (AMI) and patients that have failed PTCA (percutaneous transluminal coronary angioplasty) and have abrupt thrombotic closure of the targeted artery. The hydrogel coating on the balloon is impregnated with the thrombolytic agent by methods previously described and is introduced into the blood vessel, across the thrombus. The balloon is inflated to deliver a bolus of the agent over a short duration by compression of the hydrogel against the thrombus. Under the pressure of the application the drug enters the thrombus. This results in efficient dissolution of the thrombus, and has health and economic advantages.

To evaluate the efficacy of local delivery of urokinase during balloon angioplasty in treating intracoronary thrombus according to the invention, 11 patients were treated with hydrogel-coated balloons which had been immersed in a concentrated solution of urokinase (50,000 units/ml). Eight patients presented with acute myocardial infarctions, while the remaining three had unstable angina. Five patients had received intravenous thrombolytic therapy, including systemic thrombolysis. Conventional balloon angioplasty was initially performed in 9 of the 11 patients and was complicated either by acute thrombotic closure (n=7) or slow antegrade flow with the appearance of intracoronary thrombus (n=2). The remaining 2 patients had coronary stenoses with angiographic evidence of thrombus, but were not initially treated with conventional angioplasty. In all 11 patients, subsequent balloon dilatation at pressure in excess of 2 atmospheres with a urokinase-impregnated, hydrogel-coated balloon (1–2 inflations, inflation time 1–5 minutes) resulted in reversal of abrupt closure and dissolution of intracoronary thrombus.

As is known, balloon dilation of thrombus-containing coronary stenoses is associated with an increased risk of acute thrombotic occlusion. As a second step, following the thrombolytic therapy just described, heparin is delivered locally to the site by short-term compression of a heparin-laden, hydrogel-coated balloon to reduce the risk of further thrombotic occlusion. In alternative treatments, combination drugs may be employed. Thus, at the time of application of a thrombolytic agent, an anti thrombogenic agent or antiproliferative agent or both may be combined and administered simultaneously with the thrombolytic agent. Similarly, an anti-thrombogenic and anti-proliferative drug can be administered by incorporation in a single hydrogel coating.

Another important aspect of the invention is local intracellular pressurized delivery of bioengineered agents. Previous reference has been made to delivery of monoclonal antibodies to a selected site by compression of the hydrogel according to the invention. For example, antibodies to bFGF, PDGF, EGF, IGF and others ("Proceedings of the Restenosis Summit IV", 1992, *Science*, Vol. 253, Sep. 6, 1991, page 1129). Additionally, gene therapy for specific antithrombus and antiproliferative applications is performed using the described technique. By use of short duration compression of the gene-laden hydrogel, a bolus is applied with pressure against the tissue at the selected site. Application of genetic therapy to localized site is essential to avoid detrimentally affecting non-targeted cell types. An example of a therapeutic gene for intravascular delivery is the gene construct which expresses tissue plasminogen activator (tPA) or urokinase (*Trends in Cardiovascular Medicine*, Vol. 3, No. 2, 1993, page 61). Others would include genes to produce LAL to prevent hypercholesterolemia (*Proceeding the National Academy of Science*, Vol. 90, April 1993, page 2812). This can produce a persistent thrombolytic effect. Such capability of causing transfection of genetic material into target cells by compression against the vessel of gene laden hydrogel coating has been demonstrated by delivery of the luciferase reporter gene to cells within blood vessel wall.

According to the invention, vascular gene transfer can thus be simplified by direct delivery to the cells of naked genetic material (i.e. without need for a liposomal or retroviral micro carrier). Feasibility of direct delivery to cells was tested in 3 stages using plasmid (pRSVLUC) encoding for the luciferase (LUC) reporter gene applied to the hydrogel coating on the balloon. In the first stage, experiments documented that $^{35}$S-labeled LUC DNA (mtSEM=45+/−2 mg) could be successfully applied to and maintained in the hydrogel coating on the balloon. In the second stage, pRSVLUC-laden hydrogel coating was provided on balloons of balloon catheters. These balloon catheters were inserted into rabbit carotid arteries and inflated to 8 atm for 30 or 5 min. Arteries were then immediately excised, incubated in organ culture for 3 days, and then assayed for luciferase (LUC) activity (in Turner light units (TLU)). Gene expression achieved with 5-min inflations (n=5, tissue wt=40+/−2 mg, LUC=368+/−121 TLU) was not statistically different from that observed in arteries following 30-min inflations (n=5, tissue=44+/−4 mg, LUC=154+/−60), (p=ns). In the third stage, LUC/impregnated hydrogel-coated balloons were tested by surgical insertion in rabbit in vivo. Balloon inflation (8 atm) was performed in right carotid artery for 5 or 1 min, following which the arteries were repaired. Three days later, transfected arteries were harvested and assayed for gene expression. In arteries in which the balloons were inflated for 5 minutes (n=7, tissue=46+/−2 mg) LUC=368+/−121 TLU; for arteries inflated for 1 minute (n=7, tissue=45+/−3 mg), LUC=68+/−17 TLU (p=ns). This example illustrates: 1. Successful vascular gene transfer without liposomes or retroviral vectors using genetic material impregnated into a hydrogel coating on the balloon of a standard angioplasty balloon catheter. 2. With such balloons LUC activity occurred in all (24/24; 100%) transfected arteries. 3. With such balloons, in vivo gene expression occurred quantitatively similar to that achieved under optimized conditions in organ culture.

In another preferred embodiment, genes incorporated into microcarriers such as viral vectors can be pressure-delivered by the new technique. Examples include retrovirus and adenovirus locally delivered from a hydrogel by compression of the laden hydrogel-coated balloon against the target site. Local delivery of viral vectors is advantageous for avoiding systemic toxic reactions (*Trends in Cardiovascular Medicine*, January/February 1991, page 12).

A study was designed to demonstrate percutaneous adenovirus-mediated gene transfer by the hydrogel coated balloon catheter.

For percutaneous transfections AdrSVβgal (*Proceeding the National Academy of Science*, Vol. 90, April 1993, page 2812) was impregnated into the hydrogel coating on the balloons of balloon catheters. The balloon catheters were percutaneously inserted into rabbit iliac and inflated for 30 minutes. Vascular gene expression after 3 days was observed in residual endothelial cells as well as in many subintimal smooth muscle cells and was limited to the inflation site. Efficiency of gene transfer to smooth muscle cells by this technique was observed to be increased relative to introduction into a region of iliac isolated at each side by a balloon.

A further embodiment of the invention includes drugs complexed or conjugated to selected antibodies incorporated into the hydrogel coating on the balloon and locally delivered with pressure by compression of the hydrogel against the target site for short duration.

Additionally, antisense oligonucleotides can be rapidly introduced into the target site from hydrogel coating on the balloon catheter in the manner described above.

An example is local delivery of antisense c-myb. c-myb has been shown to play an important role in the development and proliferation of smooth muscle cells. (*Nature*, Vol. 254, Sep. 3, 1993, page 67). Antisense oligonucleotides to c-myb have been shown to inhibit smooth muscle cell proliferation in-vitro, and in vivo following balloon angioplasty.

Local intramural delivery of c-myb antisense oligonucleotides was performed in normal peripheral porcine arteries using antisense-impregnated hydrogel coated balloons on balloon catheters. Femoral and carotid vessels received locally delivered antisense oligonucleotides in concentrations ranging from 25 to 200 micromoles, employing compression of the carrier hydrogel. Contralateral vessels received the complementary sense strand and served as controls. All arterial segments were surgically removed 5–7 days following angioplasty. Cellular proliferation was evaluated by immunohistochemical labelling with PC10, an antibody to PCNA (Proliferating Cell Nuclear Antigen). Nuclear staining was quantified using the Cell Analysis System. Cellular proliferation was less in antisense-treated vessels than in controls. In antisense treated vessels, 6.89+/−5.26% of nuclear area demonstrated staining for PCNA, compared to 9.35+/−5.89% in sense treated vessels (p=0.02). Staining with anti-smooth muscle actin body (1A4) suggested a smooth muscle cell origin of proliferating cells. Localized delivery of antisense oligonucleotides by this method during balloon angioplasty is thus shown to reduce the in-vivo proliferative response to vascular injury and is thus indicated to be useful in the prevention of restenosis by reducing smooth muscle cell proliferation.

Non-vascular as well as vascular applications can utilize the compressed hydrogel pressurized administration technique. These include non-vascular chemotherapeutic applications such as colorectal cancer, liver cancer, pancreatic cancer, esophageal cancer and cancers of other organs. In addition to local delivery of conventional chemotherapeutics such as methotrexate, 5 Fluorouracil, cytlochosthamide and cytaratine (*Journal of Vascular and Intraventional of Radiology*, May 1992, Vol. 3, No. 2, page 273) for these conditions, genetic material may also be delivered to tumor sites. Additionally, local delivery of antiproliferatives and genetic materials to prevent tissue proliferation in other non-vascular applications can be accomplished with this device and procedure. An example is local delivery via the hydrogel coated balloon impregnated with prostate shrinking drugs to the prostate to treat benign prostatic hyperplasia (BPH).

Previously in this text, reference has been made to local delivery concurrent with stent delivery to the vasculature from a drug-impregnated hydrogel coated balloon. A further example is pre-dilation of a site with an antithrombogenic agent such as heparin, followed by emplacement of the stent.

A further aspect of the invention is application into the hydrogel and pressurized delivery of non and slightly water-soluble drugs from the hydrogel coating in the manner described. Additionally, biodegradable or non-degradable microparticles can be applied to enter the hydrogel and be pressure-delivered from it. The drug may be encapsulated in the particles or the particles themselves may be comprised of the drug. The particles carried in the hydrogel and mobilized by fluid, e.g., body fluid are delivered rapidly by compression of the hydrogel against the vessel wall by inflation of the balloon. The effect is to impregnate the particles into the vessel wall.

Whereas the examples above have primarily emphasized administration to tissue via natural vessels and ducts of the body, the invention in its broader aspects is not so limited. For instance, a small hydrogel-coated, drug-impregnated balloon catheter can be readily introduced into solid tissue mass by percutaneous techniques. The balloon can then be inflated to eject a bolus of the drug from the hydrogel and drive it into the adjoining tissue by the pressure exerted by the balloon.

In connection with FIGS. 2 and 2a, the use of a sheath has been described above to mechanically protect drug within the hydrogel coating. Further advantageous protection of the drug-laden hydrogel will now be described.

Referring to FIG. 2b, when being prepared, a balloon 4 wrapped about the catheter 3 is introduced into the sheath 7a and allowed to exit the sheath's distal end to expose the balloon. The balloon is then slightly inflated, and submerged in the drug or the drug can be "painted" or sprayed into the hydrogel. After absorption of the drug into the substance of the hydrogel, the balloon is dried, deflated, and withdrawn back into the protective sheath 7a. To facilitate the withdrawal of the balloon back into the sheath, a slit 30, in certain instances, is incorporated in the distal end of the sheath as illustrated in FIG. 2e. FIG. 2b shows a sheath 7a which is sized to tightly surround the balloon to prevent fluid flow back through the sheath. The sheath is selected to be tight-fitting, thin-walled, flexible, non-kinking, and of low friction, biocompatible material to form a relatively tight seal with the balloon. Examples of material suitable for the sheath include polyethylene, Teflon® (duPont trademark), and polyurethanes for example Tecoflex® (Thermedics trademark).

When protected by the sheath, the assembly is inserted through the arterial system via a conventional guiding catheter 40. During the procedure, the balloon catheter is pushed beyond the distal end of the guiding catheter to reach the stenosis 5 or thrombus which may reside for instance in coronary artery. A guidewire, not shown, can be employed to guide the balloon catheter site according to well known PTCA techniques.

Referring now to FIG. 2c, the original sheath 7 described above can be utilized by simply inflating the balloon slightly to form a tight seal within the enclosing sheath. At the time of delivery, the balloon can be deflated and quickly moved out of the sheath, across the lesion and inflated to effect the pressurized delivery of the drug.

FIG. 2d illustrates a catheter having an air lock feature. In this instance, following loading of the drug into the hydrogel on the balloon, a proximal sealing adaptor 50 is tightened forming an air lock and preventing any flow back of body fluid into the sheath. Subsequently, the sheath with the balloon in place, is passed as a unit through the guiding catheter to a position just proximal of the lesion site. The adaptor 50 on the sheath is then loosened to allow the catheter to be passed out of the sheath, across the lesion and then inflated. During this time, blood is allowed to flow back past the adaptor, preventing air flow from the sheath into the vasculature.

Another method of mechanically protecting drug within the hydrogel employs coating the dried, drug-laden hydrogel coating with a water-soluble polymer material. This material is a hold-release layer. It holds the drug until it reaches the site, is progressively dissolved. After it dissolves away, it exposes the underlying hydrogel is exposed, enabling release of the drug by inflation of the balloon, to impregnate the drug into the vessel by compression of the wetted, drug-laden hydrogel against the vessel wall. Examples of suitable hold-release coatings include carbowax, gelatin, polyvinyl alcohol, polyethylene oxide and polyethylene glycol.

Additionally non-water soluble, or partially water soluble biodegradable polymers may serve the same purpose. In this instance, the biodegradable polymer is heat-activated by a heating balloon to cause it to degrade within a selected time or the heat causes swelling of the layer and the drug is accelerated in its diffusion out of the hydrogel and into the vessel wall. Examples are albumin and pluronic gel F-127 (BASF). Once the biodegradable polymer has left the balloon, the drug is then available in the hydrogel to be quickly diffused into the vessel upon inflation of the balloon.

Other embodiments are within the claims.

What is claimed is:

1. A method for rapidly delivering a drug into a tissue or occlusive formation at a desired location of a body lumen, comprising:

providing a catheter having a catheter shaft constructed for delivery to said tissue or occlusive formation, and an expandable portion mounted on said catheter shaft, said expandable portion being expandable in response to controlled inflation pressure, the expandable portion being characterized by a coating of a tenaciously adhered swellable hydrogel polymer having said drug incorporated therein, said coating, when swelled, being responsive to compressive pressure elevated above said inflation pressure, to reduce the coating thickness and forcing said drug into said tissue or occlusive formation, preparing said expandable portion by introducing said drug to said coating, positioning said expandable portion in said body lumen at the point of desired drug application, expanding said expandable portion against said tissue or occlusive formation to cause delivery of said drug to said tissue or occlusive formation in about thirty minutes or less, deflating said expandable portion, and removing said catheter from said body.

2. The method of claim 1, further comprising introducing said catheter to an artery.

3. The method of claim 1 or 2, wherein said expandable portion is adapted for application of heat to said polymer material to control the rate of administration.

4. The method of claim 1, wherein said expandable portion includes a stent, placeable in said lumen by expansion thereof.

5. The method of claim 4, including a binding of said drug and said hydrogel polymer in a coating upon said stent for slow time release of drug remaining in said hydrogel polymer on said stent after compression of said hydrogel polymer by said expansion.

6. The method of claim 4, wherein said stent is balloon-expandable stent and said expandable portion is a stent positioned about said balloon.

7. The method of claim 6, wherein said stent and balloon both include said swellable hydrogel polymer coating incorporating said drug.

8. The method of claim 1, further comprising positioning said expandable portion at a point of occlusion in a body lumen and expanding said expandable portion at pressures sufficient to simultaneously dilate said lumen and deliver said drug by compression of said hydrogel polymer coating.

9. The method of claim 1, wherein said expandable portion is an inflatable balloon expandable to pressures in the range of about 1 to 20 atmospheres.

10. The method of claim 9, further comprising delivering about 20% or more of said drug during said compression.

11. The method of claim 1, wherein said drug is delivered in about ten minutes or less.

12. The method of claim 1, wherein said hydrogel polymer is selected from the group consisting of polycarboxylic acids, cellulosic polymers, gelatin polyvinylpyrrolidone, maleic anhydride polymers, polamides, polyvinyl alcohols, and polyethylene oxides.

13. The method of claim 12 wherein said hydrogel polymer is polyacrylic acid.

14. The method of any one of claims 1, 2 or 13 wherein said drug is a monoclonal antibody.

15. The method of claim 1, wherein said drug is delivered in about fifteen minutes or less.

16. The method of claim 1, wherein said drug is delivered in about one to ten minutes.

17. The method of claim 16, wherein said drug is delivered in about one to five minutes.

18. The method of claim 1 wherein said drug is heparin.

* * * * *